United States Patent [19]

Kaitoh et al.

[11] Patent Number: 4,996,334

[45] Date of Patent: Feb. 26, 1991

[54] SORBITOL DERIVATIVES

[75] Inventors: Mitsumasa Kaitoh; Shoichiro Mori, both of Ibaraki, Japan

[73] Assignee: Mitsubishi Petrochemical Co., Ltd., Tokyo, Japan

[21] Appl. No.: 305,646

[22] Filed: Feb. 3, 1989

[30] Foreign Application Priority Data

Feb. 5, 1988 [JP] Japan .................................. 63-25434
Jun. 10, 1988 [JP] Japan .................................. 63-143059
Aug. 2, 1988 [JP] Japan .................................. 63-193266

[51] Int. Cl.$^5$ .......................................... C07D 319/04
[52] U.S. Cl. ..................................................... 549/364
[58] Field of Search ........................................ 549/364

[56] References Cited

FOREIGN PATENT DOCUMENTS 58-180488 10/1983 Japan .................................. 549/364

Primary Examiner—Nicky Chan
Attorney, Agent, or Firm—Oblon, Spivak, McClelland, Maier & Neustadt

[57] ABSTRACT

A dibenzylidenesorbitol derivative having at least one nuclear substituent selected from an ester group represented by —COOR$^1$ and an amido group represented by —CONR$^2$R$^3$, wherein R$^1$ represents a hydrocarbon group having 1 to 20 carbon atoms, and R$^2$ and R$^3$ are identical or different and each independently represents a hydrogen atom, an alkyl group, an aryl group or an aralkyl group.

6 Claims, 2 Drawing Sheets

SORBITOL DERIVATIVES

FIELD OF THE INVENTION

This invention relates to novel sorbitol derivatives. The sorbitol derivatives of the present invention have a liquid-solidifying effect, or so-called gelatinizing ability, on oils and other liquids, thereby being a valuable gelatinizer. They also have transparency- and rigidity-heightening effects on resins, a viscosity-increasing effect on coating fluids and other liquids, an emulsion-stabilizing effect and the like.

BACKGROUND OF THE INVENTION

Known sorbitol compounds in the art are dibenzylidene-sorbitol and the like, which are being used as a gelatinizer and for other purposes. A gelatinizer deprives liquids of their fluidity, thereby solidifying them into jellies, and is being employed, for example, as an oil-solidifying agent for use in the recovery of effluent oils on the sea and the coagulation treatment of waste oils, and also being used for applications in other fields such as the food and cosmetic fields.

Beside sorbitols such as dibenzylidenesorbitol, exemplary known gelatinizers include metal salts of fatty acids such as aluminum stearate; hydroxystearic acids; and amino acid derivatives such as dibutyl-N-lauroyl-glutamamide.

However, such known compounds are still insufficient in gelatinizing ability and, hence, there has been a demand in the art for a more effective gelatinizer.

SUMMARY OF THE INVENTION

It is, therefore, an object of the present invention to provide a novel sorbitol derivative having excellent gelatinizing ability not shown by the known gelatinizers.

It is another object of the present invention to provide a method for the gelatinization of nonaqueous solutions using the novel sorbitol derivative of the kind described above.

The foregoing and other objects, features and advantages of the present invention will be apparent to those skilled in the art from the following detailed description and appended claims taken in connection with the accompanying drawings in which:

DETAILED DESCRIPTION OF THE INVENTION

In one aspect of this invention, there is provided a dibenzylidenesorbitol derivative having at least one nuclear substituent selected from an ester group represented by —COOR$^1$ and an amido group represented by —CONR$^2$R$^3$, wherein R$^1$ represents a hydrocarbon group having 1 to 20 carbon atoms, and R$^2$ and R$^3$ are identical or different and each independently represents a hydrogen atom, an alkyl group, an aryl group or an aralkyl group.

The dibenzylidenesorbitol moiety constituting the basic molecular structure of the sorbitol derivatives of the present invention is equivalent to the compounds formed by the condensation of 1 mole of sorbitol and 2 moles of benzaldehyde. This condensation usually proceeds such that one benzaldehyde molecule reacts with the hydroxyl groups at the 1- and 3-positions of the sorbitol and another benzaldehyde molecule reacts with those at the 2- and 4-positions.

In the present invention, the dibenzylidenesorbitol derivative has at least one nuclear substituent selected from an ester group represented by —COOR$^1$ and an amido group represented by —CONR$^2$R$^3$. This means that plural substituents, two for example, of these kinds may be bonded to one or preferably both of the benzene rings of the benzylidene groups. In this case, the plural substituents may be identical or different. It also means that the benzene rings of the benzylidene groups may be freely substituted with any substituent for a purpose.

Therefore, exemplary dibenzylidenesorbitol derivatives according to the present invention are those represented by the following formula (I):

In the above formula (I), X$^1$ and X$^2$ each independently represents a group or atom selected from the group consisting of (1) —COOR$^1$, wherein R$^1$ stands for a hydrocarbon group having 1 to 20 carbon atoms, such as an alkyl group having 1 to 20, preferably 1 to 8, carbon atoms, an aryl group having 6 to 20, preferably 6 to 14, carbon atoms or an aralkyl group having 7 to 20, preferably 7 to 15, carbon atoms, (2) —CONR$^2$R$^3$, wherein R$^2$ and R$^3$ are identical or different and each independently represents a hydrogen atom, an alkyl group, an aryl group or an aralkyl group, (3) an alkyl group having 1 to 8, preferably 1 to 4, carbon atoms, (4) an alkoxy group having 1 to 8, preferably 1 to 4, carbon atoms, (5) a hydroxyl group, (6) a chlorine atom and (7) a hydrogen atom (i.e. unsubstituted), provided that at least one of X$^1$ and X$^2$ represents —COOR$^1$ or —CONR$^2$R$^3$. In this invention, where R$^1$, R$^2$ or R$^3$ represents an aryl group or an aralkyl group, the aryl group and the aryl moiety of the aralkyl group include alkaryl group such as, for example, a tolyl group.

Exemplary dibenzylidenesorbitol derivative according to the present invention has one X$^1$ and one X$^2$ as shown by formula (I). However, the derivative of this invention may also be that having plural X$^1$'s and X$^2$'s, unless it beyonds the scope of the invention.

The above-mentioned derivatives according to the present invention are equivalent to compounds obtained by introducing an ester group and/or an amido group into dibenzylidenesorbitol at its benzene ring(s). The introduction of such a substituent has enabled the dibenzylidenesorbitol derivatives of the present invention to have improved gelatinizing ability.

In the formula (I) mentioned above, the substituents $X^1$ and $X^2$ may be in any of the o-, m- and p-positions. Exemplary derivatives of the present invention are those with both $X^1$ and $X^2$ bonded at the p-positions.

Where $X^1$ (and $X^2$) is an ester group represented by —COOR$^1$, examples of R$^1$ include methyl, ethyl, propyl, butyl, hexyl, octyl, dodecyl, hexadecyl, cyclohexyl, phenyl, tolyl and naphthyl groups and the like.

Where $X^1$ (and $X^2$) is an amido group represented by —CONR$^2$R$^3$, R$^2$ and R$^3$ preferably stand for an hydrogen atom, an alkyl group having 1 to 20 carbon atoms, an aryl group having 6 to 20 carbon atoms and an aralkyl group having 7 to 20 carbon atoms. For example, the amido group may be unsubstituted amido ($R^2=R^3=H$), N-methylamido ($R^2=H, R^3=CH_3$), N,N dimethylamido ($R^2=R^3=CH_3$), N-ethylamido ($R^2=H, R^3=C_2H_5$), N,N-diethylamido ($R^2=R^3=C_2H_5$), N-propylamido ($R^2=H, R^3=C_3H_7$), N,N-dipropylamido ($R^2=R^3=C_3H_7$), N-octylamido ($R^2=H, R^3=C_8H_{17}$), N,N-dioctylamido ($R^2=R^3=C_8H_{17}$), N-cyclohexylamido ($R^2=H, R^3=C_6H_{11}$), N,N-dicyclohexylamido ($R^2=R^3=C_6H_{11}$), N-phenylamido ($R^2=H, R^3=C_6H_5$), N,N-diphenylamido ($R^2=R^3=C_6H_5$) or the like.

In one preferred embodiment of this invention, both $X^1$ and $X^2$ are —COOR$^1$ or —CONR$^2$R$^3$, especially —COOR$^1$. In this case, the two R$^1$'s may be identical or different, as mentioned above.

Where $X^1$ (and $X^2$) is an alkyl group, its examples include methyl, ethyl, propyl, butyl, hexyl, octyl and cyclohexyl groups and the like.

Where $X^1$ and (and $X^2$) is an alkoxy group, its examples include methoxy, ethoxy, propoxy, butoxy, hexyloxy, octyloxy, cyclohexyloxy groups and the like.

As specific examples of the dibenzylidenesorbitol derivative of the present invention, there may be mentioned as follows.

The dibenzylidenesorbitol derivatives represented by the above-mentioned formula (I) in which one of $X^1$ and $X^2$ is —COOR$^1$ and the other is a hydrogen atom include:
1,3-(p-methoxycarbonylbenzylidene) 2,4-benzylidenesorbitol,
1,3-benzylidene-2,4-(p-methoxycarbonylbenzylidene)sorbitol, and the like.

The dibenzylidenesorbitol derivatives represented by the formula (I) in which one of $X^1$ and $X^2$ is —COOR$^1$ and the other is an alkyl group include:
1,3-(p-methoxycarbonylbenzylidene)-2,4-(p-methylbenzylidene)sorbitol,
1,3-(p-methoxycarbonylbenzylidene)-2,4-(p-ethylbenzylidene)sorbitol
1,3-(p-methylbenzylidene)-2,4-(p-methoxycarbonylbenzylidene)sorbitol,
1,3 (p-ethylbenzylidene)-2,4-(p-methoxycarbonylbenzylidene)sorbitol, and the like.

The dibenzylidenesorbitol derivatives represented by the formula (I) in which one of $X^1$ and $X^2$ is —COOR$^1$ and the other is an alkoxy group include:
1,3-(p-methoxycarbonylbenzylidene)-2,4-(p-methoxybenzylidene)sorbitol,
1,3-(p-methoxybenzylidene)-2,4-(p-methoxycarbonylbenzylidene)sorbitol, and the like.

The dibenzylidenesorbitol derivatives represented by the formula (I) in which one of $X^1$ and $X^2$ is —COOR$^1$ and the other is a hydroxyl group include:
1,3-(p methoxycarbonylbenzylidene)-2,4-(p-hydroxylbenzylidene)sorbitol,
1,3-(p-hydroxybenzylidene)-2,4-(p-methoxycarbonylbenzylidene)sorbitol, and the like.

The dibenzylidenesorbitol derivatives represented by the formula (I) in which one of $X^1$ and $X^2$ is —COOR$^1$ and the other is a chlorine atom include:
1,3-(p-methoxycarbonylbenzylidene)-2,4 (p-chlorobenzylidene)sorbitol,
1,3-(p-chlorobenzylidene)-2,4-(p-methoxycarbonylbenzylidene)sorbitol, and the like.

The dibenzylidenesorbitol derivatives represented by the formula (I) in which both $X^1$ and $X^2$ are —COOR$^1$include:
1,3:2,4-bis(p-carboxybenzylidene)sorbitol,
1,3:2,4-bis(p-methoxycarbonylbenzylidene)sorbitol,
1,3:2,4-bis(p-ethoxycarbonylbenzylidene)sorbitol,
1,3:2,4-bis(p-n-propoxycarbonylbenzylidene)sorbitol,
1,3:2,4-bis(p-isopropoxycarbonylbenzylidene)sorbitol,
1,3:2,4-bis(p-n-butoxycarbonylbenzylidene)sorbitol,
1,3:2,4-bis(p-isobutoxycarbonylbenzylidene)sorbitol,
1,3:2,4-bis(p-sec-butoxycarbonylbenzylidene)sorbitol,
1,3:2,4-bis(p-tert-butoxycarbonylbenzylidene)sorbitol,
1,3:2,4-bis(p-n-hexyloxycarbonylbenzylidene)sorbitol,
1,3:2,4-bis(p-cyclohexyloxycarbonylbenzylidene)sorbitol,
1,3:2,4-bis(p-n-octyloxycarbonylbenzylidene)sorbitol,
1,3:2,4-bis(p-2'-ethylhexyloxycarbonylbenzylidene) sorbitol,
1,3:2,4-bis(p-n-dodecyloxycarbonylbenzylidene)sorbitol,
1,3:2,4-bis(p-n-hexadecyloxycarbonylbenzylidene)sorbitol,
1,3:2,4-bis(p-phenoxycarbonylbenzylidene)sorbitol,
1,3:2,4-bis(p-phenylethoxycarbonylbenzylidene)sorbitol,
1,3:2,4-bis(m-carboxybenzylidene)sorbitol,
1,3:2,4-bis(m-methoxycarbonylbenzylidene)sorbitol,
1,3:2,4-bis(m-ethoxycarbonylbenzylidene)sorbitol,
1,3:2,4-bis(m-n-propoxycarbonylbenzylidene)sorbitol,
1,3:2,4-bis(m-isopropoxycarbonylbenzylidene)sorbitol,
1,3:2,4-bis(m-cyclohexyloxycarbonylbenzylidene)sorbitol,
1,3:2,4-bis(m-phenoxycarbonylbenzylidene)sorbitol,
1,3:2,4-bis(o-carboxybenzylidene)sorbitol,
1,3:2,4-bis(o-methoxycarbonylbenzylidene)sorbitol,
1,3-p-carboxybenzylidene-2,4-p-methoxycarbonylbenzylidenesorbitol,
1,3-p-carboxybenzylidene-2,4-p-ethoxycarbonylbenzylidenesorbitol,
1,3-p-carboxybenzylidene-2,4-p-n butoxycarbonylbenzylidenesorbitol,
1,3-p-carboxybenzylidene-2,4-p-cyclohexyloxycarbonylbenzylidenesorbitol,
1,3-p-methoxycarbonylbenzylidene-2,4-p-carboxybenzylidenesorbitol,
1,3-p-methoxycarbonylbenzylidene-2,4-p-ethoxycarbonylbenzylidenesorbitol,
1,3-p-methoxycarbonylbenzylidene-2,4-p-n-butoxycarbonylbenzylidenesorbitol,
1,3-p-methoxycarbonylbenzylidene-2,4-p-cyclohexyloxycarbonylbenzylidenesorbitol, 1,3-p-ethoxycarbonylbenzylidene-2,4-p-carbonylbenzylidenesorbitol,
1,3-p-ethoxycarbonylbenzylidene-2,4-p-methoxycarbonylbenzylidenesorbitol,
1,3-p-ethoxycarbonylbenzylidene-2,4-p-n-butoxycarbonylbenzylidenesorbitol,
1,3-p-ethoxycarbonylbenzylidene-2,4-p cyclohexyloxybenzylidenesorbitol,
1,3-p-n-butoxycarbonylbenzylidene-2,4-p-carboxybenzylidenesorbitol,
1,3-p-n butoxycarbonylbenzylidene-2,4-p-methoxycarbonylbenzylidenesorbitol,
1,3-p n-butoxycarbonylbenzylidene-2,4-p-ethoxycarbonylbenzylidenesorbitol,
1,3-p n-butoxycarbonylbenzylidene-2,4-p-cyclohexyloxycarbonylbenzylidenesorbitol,
1,3-p-cyclohexyloxycarbonylbenzylidene-2,4-p-carboxybenzylidenesorbitol,
1,3-p-cyclohexyloxycarbonylbenzylidene-2,4-p-methoxycarbonylbenzylidenesorbitol,
1,3-p-cyclohexyloxycarbonylbenzylidene-2,4-p-ethoxycarbonylbenzylidenesorbitol,
1,3-p-cyclohexyloxycarbonylbenzylidene-2,4-p-n-butoxycarbonylbenzylidenesorbitol, and the like.

The dibenzylidenesorbitol derivatives represented by the formula (I) in which both $X^1$ and $X^2$ are —$CONR^2R^3$ and identical include:
1,3:2,4-bis(p-carbamoylbenzylidene)sorbitol,
1,3:2,4-bis(p-N-methylcarbamoylbenzylidene)sorbitol,
1,3:2,4-bis(p-N,N-dimethylcarbamoylbenzylidene)sorbitol,
1,3:2,4-bis(p-N-ethylcarbamoylbenzylidene)sorbitol,
1,3:2,4-bis(p-N,N-diethylcarbamoylbenzylidene)sorbitol,
1,3:2,4-bis(p-N-propylcarbamoylbenzylidene)sorbitol,
1,3:2,4-bis(p-N,N-dipropylcarbamoylbenzylidene)sorbitol,
1,3:2,4-bis(p-N-cyclohexylcarbamoylbenzylidene)sorbitol,
1,3:2,4-bis(p-N,N-dicyclohexylcarbamoylbenzylidene)sorbitol,
1,3:2,4-bis(p-N-phenylcarbamoylbenzylidene)sorbitol,
1,3:2,4-bis(p-N,N-diphenylcarbamoylbenzylidene)sorbitol, and the like.

The dibenzylidenesorbitol derivatives represented by the formula (I) in which both $X^1$ and $X^2$ are —$CONR^2R^3$ but different include:
1,3-(p-carbamoylbenzylidene)-2,4-(p N-methylcarbamoylbenzylidene)sorbitol,
1,3-(p-carbamoylbenzylidene)-2,4-(p-N,N-dimethylcarbamoylbenzylidene)sorbitol,
1,3-(p-carbamoylbenzylidene)-2,4-(p-N-propylcarbamoylbenzylidene)sorbitol,
1,3-(p-N-methylcarbamoylbenzylidene)-2,4-(p-carbamoylbenzylidene)sorbitol,
1,3-(p-N-methylcarbamoylbenzylidene)-2,4-(p-N,N-dimethylcarbamoylbenzylidene)sorbitol,
1,3-(p-N-methylcarbamoylbenzylidene)-2,4-(p-N-propylcarbamoylbenzylidene)sorbitol,
1,3-(p-N-methylcarbamoylbenzylidene)-2,4-(p-N-cyclohexylcarbamoylbenzylidene)sorbitol,
1,3-(p-N-methylcarbamoylbenzylidene)-2,4-(p-N-phenylcarbamoylbenzylidene)sorbitol,
1,3-(p N,N-dimethylcarbamoylbenzylidene)-2,4-(p-carbamoylbenzylidene)sorbitol,
1,3-(p-N,N-dimethylcarbamoylbenzylidene)-2,4-(p-N-methylcarbamoylbenzylidene)sorbitol,
1,3-(p-N-propylcarbamoylbenzylidene)-2,4-(p-carbamoylbenzylidene)sorbitol,
1,3-(p-N-propylcarbamoylbenzylidene)-2,4-(p-N-methylcarbamoylbenzylidene)sorbitol,
1,3-(p-N-cyclohexylcarbamoylbenzylidene)-2,4-(p-N-methylcarbamoylbenzylidene)sorbitol,
1,3-(p-N-phenylcarbamoylbenzylidene)-2,4-(p-N-methylcarbamoylbenzylidene)sorbitol, and the like.

The dibenzylidenesorbitol derivatives represented by the formula (I) in which one of $X^1$ and $X^2$ is —$CONR^2R^3$ and the other is a hydrogen atom include:
1,3-(p-N-methylcarbamoylbenzylidene)-2,4-benzylidenesorbitol,
1,3-benzylidene-2,4-(p-N-methylcarbamoylbenzylidene) sorbitol,
1,3-(p-N-propylcarbamoylbenzylidene)-2,4-benzylidenesorbitol,
1,3-(p-N-cyclohexylcarbamoylbenzylidene)-2,4-benzylidenesorbitol,
1,3-(p-N-phenylcarbamoyl)-2,4-benzylidenesorbitol, and the like.

The dibenzylidenesorbitol derivatives represented by the formula (I) in which one of $X^1$ and $X^2$ is $CONR^2R^3$ and the other is an alkyl group include:
1,3-(p-carbamoylbenzylidne)-2,4-(p-methylbenzylidene)sorbitol,
1,3-(p-N methylcarbamoylbenzylidene)-2,4-(p-methylbenzylidene)sorbitol,
1,3-(p-methylbenzylidene)-2,4-(p-N-methylcarbamoylbenzylidene)sorbitol,
1,3-(p-N methylcarbamoylbenzylidene)-2,4-(p-ethylbenzylidene)sorbitol,
1,3-(p-N-methylcarbamoylbenzylidene)-2,4-(p-butylbenzylidene)sorbitol,
1,3-(p-N-propylcarbamoylbenzylidene)-2,4-(p methylbenzylidene)sorbitol,
1,3-(p-N-cyclohexylcarbamoylbenzylidene)-2,4-(p-methylbenzylidene)sorbitol,
1,3-(p-N-phenylcarbamoylbenzylidene)-2,4-(p-methylbenzylidene)sorbitol, and the like.

The dibenzylidenesorbitol derivatives represented by the formula (I) in which one of $X^1$ and $X^2$ is —$CONR^2R^3$ and the other is an alkoxy group include:
1,3-(p-carbamoylbenzylidene)-2,4-(p-methoxybenzylidene)sorbitol,
1,3-(p-N-methylcarbamoylbenzylidene)-2,4-(p-methoxybenzylidene)sorbitol,
1,3-(p-methoxybenzylidene)-2,4-(p-N-methylcarbamoylbenzylidene)sorbitol,
1,3-(p-N-methylcarbamoylbenzylidene)-2,4-(p-ethoxybenzylidene)sorbitol,
1,3-(p-N methylcarbamoylbenzylidene)-2,4-(p-butoxybenzylidene)sorbitol,
1,3-(p-N-propylcarbamoylbenzylidene)-2,4-(p-methoxybenzylidene)sorbitol,
1,3-(p-N-cyclohexylcarbamoylbenzylidene)-2,4-(p-methoxybenzylidene)sorbitol,
1,3-(p-N-phenylcarbamoylbenzylidene)-2,4-(p-methoxybenzylidene)sorbitol, and the like.

The dibenzylidenesorbitol derivatives represented by the formula (I) in which one of $X^1$ and $X^2$ is —$CONR^2R^3$ and the other is a hydroxyl group include:
1,3-(p-N-methylcarbamoylbenzylidene)-2,4-(p-hydroxybenzylidene)sorbitol,
1,3-(p-hydroxybenzylidene)-2,4-(p-N-methylcarbamoylbenzylidene)sorbitol, and the like.

The dibenzylidenesorbitol derivatives represented by the formula (I) in which one of $X^1$ and $X^2$ is —$CONR^2R^3$ and the other is a chlorine atom include:

1,3-(p-N-methylcarbamoylbenzylidene)-2,4 (p-chlorobenzylidene)sorbitol,

1,3-(p-chlorobenzylidene)-2,4-(p-N-methylcarbamoylbenzylidene)sorbitol, and the like.

Of the above-mentioned dibenzylidenesorbitol derivatives represented by the formula (I) in which at least one of $X^1$ and $X^2$ are —$CONR^2R^3$, preferred are those in which both $X^1$ and $X^2$ are $CONR^2R^3$ and those in which one of them is —$CONR^2R^3$ and the other is a hydrogen atom or an alkyl group. Of these, especially preferred are those in which one of $X^1$ and $X^2$ is an N-(lower alkyl)carbamoyl group and the other is a hydrogen atom or an alkyl group.

The sorbitol derivatives according to the present invention may be prepared, for example, by the following methods.

The dibenzylidenesorbitol derivatives represented by the formula (I) in which $X^1$ and $X^2$ are identical and both are —$COOR^1$ may be prepared by carrying out the water-eliminating condensation reaction of sorbitol and 2 mols of formylbenzoic acid or a formylbenzoic acid ester per mol of the sorbitol, in the presence of an acid catalyst, as shown by the following reaction formula.

The formylbenzoic acid or formylbenzoic acid ester may be used in an amount of from 1.0 to 3.0 mole equivalents per mole of the sorbitol. As a catalyst, an acid such as hydrochloric acid, sulfuric acid, p-toluenesulfonic acid or the like may be used in an amount of from 0.5 to 10 mol % based on the amount of the sorbitol. As a solvent, use may be made of an organic solvent such as benzene, toluene, cyclohexane, a dialkyl ether or the like, or a mixed solvent composed of such an organic solvent and water, and the amount of the solvent may be 0.2 to 50 times by weight that of the sorbitol. The reaction temperature may be from 40° to 100° C., and the reaction time may be about 3 to 12 hours.

The dibenzylidenesorbitol sorbitol derivatives represented by the formula (I) in which $X^1$ and $X^2$ are different may be prepared, for example, through the reactions as shown below.

Illustratively stated, solbitol is reacted with an equimolar amount of a benzaldehyde derivative represented by to obtain a compound (II) as a condensation product. Then the compound (II) is reacted with an equimolar amount of a benzaldehyde derivative represented by to obtain a compound of formula [I], as a condensation product, according to the present invention. In the above reaction formulae, $X^1$ and $X^2$ are as defined hereinbefore with respect to formula [I], and either of the benzaldehyde derivatives has a substituent which is —$COOR^1$ or —$CONR^2R^3$. Further, the above two-step reaction may also be carried out successively in one reactor without isolation of the compound [II], thereby to obtain the compound [I] of the present invention.

In step (1) above, the benzaldehyde derivative may be used in an amount of from 0.8 to 1.1 mole equivalent per mole of the sorbitol. As a catalyst, an acid such as hydrochloric acid, sulfuric acid, p-toluenesulfonic acid or the like may be used in an amount of from 0.5 to 10 mol % based on the amount of the sorbitol. As a solvent, use may be made of water or a mixed solvent composed of water and a water-miscible organic solvent such as dioxane, tetrahydrofuran and the like, and the amount of the solvent may be 0.2 to 50 times by weight that of the sorbitol. The reaction temperature may be from 20 to 60° C., and the reaction time may be about 3 to 12 hours.

In step (2) above, the benzaldehyde derivative may be used in an amount of from 0.8 to 1.1 mole equivalent per mole of the compound [II]. As a catalyst, an acid such as hydrochloric acid, sulfuric acid, p-toluenesulfonic acid or the like may be used in an amount of from 0.5 to 10 mol % based on the amount of the compound [II]. As a solvent, use may be made of an organic solvent such as benzene, toluene, cyclohexane, a dialkyl ether or the like or a mixed solvent composed of such an organic solvent and water. The amount of the solvent may be 0.2 to 50 times by weight that of the compound [II]. The reaction temperature may be from 40° to 100° C., and the reaction time may be about 3 to 12 hours. The NMR spectral analysis of the compound [II] revealed that in step (1), condensation proceeds selectively in such a manner that the sorbitol reacts with the benzaldehyde derivative at the 2- and 4-positions, as shown by the reaction formula.

The dibenzylidenesorbitol derivative of the present invention has excellent gelatinizing ability, so that oils and organic solvents can be gelatinized by only a small amount of the dibenzylidenesorbitol derivative as compared with conventional gelatinizers. Especially, due to its remarkable gelatinizing ability not shown by the conventional gelatinizers, the dibenzylidenesorbitol derivative of the present invention can gelatinize even a highly polar organic solvent such as N,N-dimethylformamide, dimethyl sulfoxide or the like. Further, although conventional gelatinizers having relatively high gelatinizing ability are generally poor in solubility, the dibenzylidenesorbitol derivative of the present invention has excellent solubility, which is one of the characteristic features of the dibenzylidenesorbitol derivative according to the present invention. Hence, besides being used in usual ways as a gelatinizer, the dibenzylidenesorbitol derivative of the present invention can be employed for the gelatinization of nonaqueous electrolytes to be used in electrochemical devices such as, for example, an electrolytic capacitor, an electric double-layer capacitor, a lithium primary cell and secondary cell, a polymer cell and an electrochromic display, thereby to prevent leakage of the electrolytes and improve their working properties. Thus, the gelatinization of such electrolytes by the dibenzylidenesorbitol derivative of the present invention can meet the demand in the recent trend to miniature, light-weight, thin and layer-built devices. Therefore, the dibenzylidenesorbitol derivative of this invention is of great practical value in applications in the industrial field.

In another aspect of the present invention, there is provided a method for the gelatinization of nonaqueous solution, which comprises adding to said solutions a dibenzylidenesorbitol derivative having at least one nuclear substituent selected from an ester group represented by —COOR$^1$ and an amido group represented by —CONR$^2$R$^3$, wherein R$^1$ represents a hydrocarbon group having 1 to 20 carbon atoms, and R$^2$ and R$^3$ are identical or different and each independently represent a hydrogen atom or a hydrocarbon group having 1 to 20 carbon atoms.

The amount of the dibenzylidenesorbitol derivative is not especially limited if its effect is produced. When the dibenzylidenesorbitol derivative is used for the gelatinization of a nonaqueous electrolyte, its amount can be decided taking into consideration the balance between the desired electrical conductivity and the mechanical strength of the gel, and others. However, the amount of the dibenzylidenesorbitol derivative may generally be in the range of from about 0.5 to about 20% by weight, preferably from 1 to 10% by weight, based on the amount of the electrolyte.

This invention will now be described in more detail with reference to the following Examples and Application Examples but they should not be construed to be limiting the scope of the present invention.

EXAMPLE 1

Preparation of 1,3-(p-methoxycarbonylbenzylidene)-2,4-benzylidenesorbitol

Into a 200 ml flask were introduced 36.4 g (0.2 mol) of D-sorbitol, 24 ml of water, 21.2 g (0.2 mol) of benzaldehyde and 2.3 g (0.012 mol) of p-toluenesulfonic acid monohydrate, and the resulting mixture was stirred at 35° C. for 6 hours under a nitrogen atmosphere. Then, the reaction mixture was cooled to 20° C. To the resulting reaction mixture in its white creamy state were added 100 ml of water and 0.5 g of sodium hydroxide, and the resulting mixture was stirred at room temperature. The resulting white slurry was filtered to obtain a white solid. The white solid obtained was washed thoroughly with water and ether, and dried, thereby obtaining 46.4 g of 2,4-benzylidenesorbitol as a white powder in a yield of 85.9%.

Next, 46.4 g (0.17 mol) of the above obtained 2,4-benzylidenesorbitol, 27.9 g (0.17 mol) of methyl p-formylbenzoate, 800 ml of benzene and 0.32 g (1.7 mmol) of p-toluenesulfonic acid monohydrate were introduced into a 2-liter flask equipped with a Dean-Stark-type fractionating column and a powerful stirrer, and the resulting mixture was heated, with stirring, under reflux of the benzene at 77° C. for 6 hours under a nitrogen atmosphere. During the reaction, the water distilled out in the fractionating column was removed occasionally. After completion of the reaction, the reaction mixture was cooled to room temperature. Subsequently, to the resulting reaction mixture in its white gelatinous state were added 300 ml of water and 70 mg of sodium hydroxide, and the mixture was then stirred at room temperature. The resulting white slurry was filtered to obtain a white solid. The white solid thus obtained was washed with water and ethanol each having a temperature of about 70° C. and dried, thereby obtaining 65.8 g of the intended compound, 1,3-(p-methoxycarbonylbenzylidene)-2,4-benzylidenesorbitol, as a white power in a yield of 92.0%. The yield calculated on the basis of the D-sorbitol was 79.0%.

This compound was analyzed, giving the following data:

Melting point 204.0°–208.5° C.

$^1$H-NMR spectrum (DMSO-d$_6$) δ [ppm]: 7.98(2H, d), 7.61(2H, d), 7.44–7.48(2H, m), 7.35–7.39 (3H, m), 5.76(1H, s), 5.67(1H, s), 4.81(1H, d), 4.77(1H, t), 3.45–4.36(8H, m), 3.86(3H, s).

Mass spectrum m/e (relative intensity): 416(4.0, M+), 385(3.5), 355(6.8), 267(6.8), 207(14), 149(78), 105(100), 91(76), 77(35).

EXAMPLE 2

Preparation of 1,3 (p-methoxycarbonylbenzylidene)-2,4-(p-methylbenzylidene)sorbitol Using 54.6 g (0.3 mol) of D-sorbitol, 36 ml of water, 36.0 g (0.3 mol) of p-tolualdehyde and 3.4 g (0.018 mol) of p-toluenesulfonic acid monohydrate, the same procedures as in Example 1 were repeated, thereby obtaining 75.5 g of 2,4-(p-methylbenzylidene)sorbitol as a white powder in a yield of 88.6%.

Next, using 75.5 g (0.27 mol) of 2,4-(p-methylbenzylidene)sorbitol, 44.3 g (0.27 mol) of methyl p-formylbenzoate, 1200 ml of benzene and 0.51 g (2.7 mmol) of p-toluenesulfonic acid monohydrate, the same procedures as in Example 1 were repeated, thereby obtaining 107.4 g of 1,3-(p-methoxycarbonylbenzylidene)-2,4-(p-methylbenzylidene)sorbitol as a white powder in a yield of 94.0%. The yield calculated on the basis of the D-sorbitol was 83.3%.

This compound was analyzed, giving the following data:

Melting point 216.0°-219.0° C.

$^1$H-NMR spectrum (DMSO-$d_6$) δ [ppm]: 7.99(2H, d), 7.61(2H, d), 7.35(2H, d), 7.19(2H, d), 5.75(1H, s), 5.62(1H, s), 4.81(1H, d), 4.77(1H, t), 3.41–4.37(8H, m), 3.87(3H, s), 2.30(3H, s).

Mass spectrum m/e (relative intensity): 430(8.1, M$^+$), 399(3.5), 369(6.2), 250(4.3), 207(23), 163(49), 119(100), 105(57).

APPLICATION EXAMPLES 1 AND 2 AND COMPARATIVE EXAMPLE 1

Each of the compounds of the present invention as obtained in Examples 1 and 2 and a comparative compound, 1,3:2,4-dibenzylidenesorbitol, was added to γ-butyrolactone in prescribed various amounts, and the resulting mixtures were heated to dissolve the compounds. The solutions thus obtained were cooled to room temperature and allowed to stand overnight, to form gels. The minimum concentration of each compound required for gelatinization, and the temperature and time needed to dissolve each compound are shown in Table 1 together with the appearances of the gels.

TABLE 1

| Compound | | Minimum concentration required for gelatinization | Temperature and time for dissolving | Appearance of gel |
|---|---|---|---|---|
| Application Example 1 | 1,3-(p-methoxycarbonylbenzylidene)-2,4-benzylidenesorbitol | 1 wt % | 65° C. 1 hr | colorless transparent gel |
| Application Example 2 | 1,3-(p-methoxycarbonylbenzylidene)-2,4-(p-methylbenzylidene)sorbitol | 1 wt % | 70° C., 1 hr | colorless transparent gel |
| Comparative Example 1 | 1,3:2,4-dibenzylidenesorbitol | 10 wt % | 65° C., 1 hr | white turbid gel |

APPLICATION EXAMPLES 3 AND 4 AND COMPARATIVE EXAMPLE 2

The same procedures as in Application Examples 1 and 2 and Comparative Example 1 were repeated except that N,N-dimethylformamide was used in place of Γ-butyrolactone, to form gels. The results obtained are shown in Table 2. In Comparative Example 2, 1,3:2,4-dibenzylidenesorbitol could not form gels even when its concentration was as high as 10%.

TABLE 2

| Compound | | Minimum concentration required for gelatinization | Temperature and time for dissolving | Appearance of gel |
|---|---|---|---|---|
| Application Example 3 | 1,3-(p-methoxycarbonylbenzylidene)-2,4-benzylidenesorbitol | 2 wt % | 65° C., 0.5 hr | colorless transparent gel |
| Application Example 4 | 1,3-(p-methoxycarbonylbenzylidene)-2,4-(p-methylbenzylidene)sorbitol | 2 wt % | 70° C., 0.5 hr | colorless transparent gel |
| Comparative Example 2 | 1,3:2,4-dibenzylidenesorbitol | 10 wt % | 65° C., 0.5 hr | no gel formed |

EXAMPLE 3

Preparation of 1,3:2,4-bis(p-carboxybenzylidene)sorbitol

Into a 2-liter flask equipped with a Dean-Stark-type fractionating column and a powerful stirrer were introduced 54.6 g (0.3 mol) of D-sorbitol and 36 ml of water, and the resulting mixture was stirred at room temperature. To this mixture were added 90 g (0.6 mol) of p-formylbenzoic acid, 800 ml of isopropyl alcohol and 300 ml of cyclohexane, and the resulting mixture was stirred under a nitrogen atmosphere. 2.7 g (27 mmol) of concentrated sulfuric acid was added thereto, and the resulting mixture was stirred under reflux for 6 hours. Then, after being cooled, the thus-obtained reaction mixture in its white gelatinous state was neutralized with an aqueous sodium hydroxide solution, and then the isopropyl alcohol and the cyclohexane were removed under reduced pressure. Subsequently, water was added to the resulting mixture. This mixture was stirred thoroughly and then filtered, to obtain a white solid. This white solid was washed with methanol, filtered and then dried, thereby obtaining 115.7 g of a white powdery solid. Upon analysis, this solid was found to be the intended compound. The yield was 86.5%. The analytical data for this compound were as follows:

Melting point 285.0°-287.0° C.

$^1$H-NMR spectrum (DMSO-$d_6$) γ [ppm]: 7.95(4H, d), 7.60(4H, d), 5.75(2H, s), 3.40– 4.60(12H, m).

$^{13}$C-NMR spectrum (DMSO-$d_6$) δ [ppm]:

167.1 (—C(=O)—O), 142.7 and 142.4

131.4

-continued 129.0 and 128.9 (  ), 126.6 and 126.1 (  ), 98.6 (  ), 77.6, 70.1, 68.5 and 67.7 (—CH—), 69.0 and 62.5 (—CH$_2$O—).

Mass spectrum m/e (relative intensity): 446(3.5, M+), 445(1.8), 428(1.9), 296(2.7) 193(8.1), 150(62), 149(100), 135(15), 121(34), 65(27).

EXAMPLE 4

Preparation of 1,3:2,4-bis(p-methoxycarbonylbenzylidene)sorbitol

Into a 1-liter flask equipped with a Dean-Stark-type fractionating column and a powerful stirrer were introduced 13.7 g (75 mmol) of D-sorbitol, 24.6 g (150 mmol) of methyl p-formylbenzoate, 400 ml of benzene and 290 mg (1.5 mmol) of p-toluenesulfonic acid monohydrate, and the resulting mixture was stirred under a nitrogen atmosphere. After being stirred under reflux for 4 hours and then cooled, the reaction mixture in its white gelatinous state was neutralized with an aqueous sodium hydroxide solution, and the benzene was removed under reduced pressure. Subsequently, water was added to the resulting mixture. This mixture was stirred thoroughly and then filtered, to obtain a white solid. This white solid was washed with ethanol, filtered and then dried, thereby obtaining 32.6 g of the intended compound as a white powdery solid in a yield of 91.6%. The analytical data for this compound were as follows:

Melting point 223.5°-226.0° C.

$^1$H-NMR spectrum (DMSO-d$_6$) δ [ppm]: 7.95(4H, d), 7.55(4H, d), 4.75(1H, d), 4.35(1H, t), 3.85(6H, s), 3.40–4.25(8H, m).

$^{13}$C-NMR spectrum (DMSO-d$_6$) δ [ppm]:

165.9 (—C(=O)—O—), 143.3 and 143.0 (  )

129.8 and 129.7 (  ), 128.9 and 128.8 (  ), 126.4 (  ), 98.5 and 98.4 (  ), 77.6, 70.1, 68.5 and 67.6 (—CH—), 69.3 and 62.5 (—CH$_2$O—), 52.0 (—OCH$_3$).

Mass spectrum m/e (relative intensity): 474(6.8, M+), 473(6.8), 443(15), 382(6.8), 250(27), 207(54), 165(97), 163(100), 149(62), 133(51), 105(45), 77(22), 59(22).

EXAMPLE 5

Preparation of 1,3:2,4-bis(p-n-butoxycarbonylbenzylidene)sorbitol

Into a 200-ml flask equipped with a Dean-Stark-type fractionating column and a powerful stirrer were introduced 3.64 g (20 mmol) of D-sorbitol, 8.24 g (40 mmol) of butyl p-formylbenzoate, 80 ml of benzene and 60 mg (0.32 mmol) of p-toluenesulfonic acid monohydrate, and the same procedures as in Example 4 were repeated. Thus, 10.1 g of a white powdery solid having a melting point of 192.5°-197.0° C. was obtained. The $^1$H-NMR spectral, $^{13}$C-NMR spectral and mass spectral data revealed that this solid was the intended compound. The yield was 90.5%.

APPLICATION EXAMPLE 5

In 100g of N,N-dimethylformamide was dissolved at 100° C. 4 g of 1,3:2,4-bis(p-carboxybenzylidene)sorbitol. The resulting solution was cooled to room temperature and allowed to stand overnight, thereby obtaining a gel of N,N dimethylformamide.

APPLICATION EXAMPLE 6

In 100 g of N,N-dimethylformamide was dissolved at 100° C. 2 g of 1,3:2,4-bis(p-methoxycarbonylbenzylidene)sorbitol. The resulting solution was cooled to room temperature and allowed to stand for an hour, thereby obtaining an almost transparent gel of N,N-dimethylformamide.

APPLICATION EXAMPLE 7

In 100 g of N,N-dimethylformamide was dissolved at 100° C. 1 g of 1,3:2,4-bis(p-methoxycarbonylbenzylidene)sorbitol. The resulting solution was cooled to room temperature and allowed to stand overnight, thereby obtaining a transparent gel of N,N-dimethylformamide.

APPLICATION EXAMPLE 8

In 100 g of dimethyl sulfoxide was dissolved at 100° C. 2 g of 1,3:2,4-bis(p-methoxycarbonylbenzylidene)-sorbitol. The resulting solution was cooled to room temperature and allowed to stand overnight, thereby obtaining a transparent gel of dimethyl sulfoxide.

APPLICATION EXAMPLE 9

To 100 g of ethanol was added 0.1 g of 1,3:2,4- bis(p-methoxycarbonylbenzylidene)sorbitol. The resulting mixture was allowed to stand overnight, thereby obtaining an almost transparent gel of ethanol.

APPLICATION EXAMPLE 10

In 100 g of N,N-dimethylformamide was dissolved at 100° C. 1 g of 1,3:2,4-bis(p-n-butoxycarbonylbenzylidene)sorbitol. The resulting solution was cooled to room temperature and allowed to stand for two hours, thereby obtaining a white gel of N,N-dimethylformamide.

Preparation of 1,3:2,4-bis(p-N-cyclohexylcarbamoyl-benzylidene)sorbitol

Into a 1-liter flask equipped with a Dean-Stark-type fractionating column and a powerful stirrer were introduced 7.4 g (40.7 mmol) of D-sorbitol, 18.8 g (81.4 mmol) of p-(N-cyclohexylcarbamoyl)benzaldehyde, 300 ml of benzene and 160 mg (0.84 mmol) of p-toluenesulfonic acid monohydrate. The resulting mixture was heated, with stirring, under reflux of the benzen at 77° C. for 7 hours under a nitrogen atmosphere. During the reaction, the water distilled out in the fractionating column was removed occasionally. After completion of the reaction, the reaction mixture was cooled to room temperature, neutralized with an aqueous sodium hydroxide solution, and then filtered, to obtain a white solid. This white solid was washed with water and ethanol each having a temperature of about 70° C., and dried, thereby obtaining 21.9 g of the intended compound, 1,3:2,4-bis(p-N-cyclohexylcarbamoyl-benzylidene)sorbitol, as a white power in a yield of 88.5%.

The analytical data for this compound were as follows:

Melting point 232.0–236.0° C.

$^1$H-NMR spectrum (DMSO-$d_6$) $\delta$ [ppm]: 8.12–8.16(2H, m), 7.78–7.87(4H, m), 7.47–7.59(4H, m), 5.75–6.08(2H, m), 5.28(1H, d), 4.91(1H, t), 3.61–4.52(8H, m), 3.76(2H, broad-s), 1.12–1.81(20H, broad-m).

FAB-Mass spectrum m/e: 609 (MH+)

EXAMPLE 7

Preparation of 1,3:2,4-bis(p-N-isopropylcarbamoylbenzylidene)sorbitol

Using 5.5 g (30 mmol) of D-sorbitol, 11.5 g (60 mmol) of p (N-isopropylcarbamoyl)benzaldehyde, 240 ml of benzene and 170 mg (0.9 mmol) of p-toluenesulfonic acid monohydrate, the same procedures as in Example 6 were repeated, thereby obtaining 13.1 g of 1,3:2,4-bis(p-N-isopropylcarbamoylbenzylidene)sorbitol as a white power in a yield of 82.7%.

The analytical data for this compound were as follows:

Melting point 239.0–242.0° C.

$^1$H-NMR spectrum (DMSO-$d_6$) $\delta$ [ppm]: 8.15–8.17(2H, m), 7.84–7.89(4H, m), 7.49–7.57(4H, m), 5.75–5.93(2H, m), 4.06–4.22(10H, m), 1.16–1.18(12H, m).

FAB-Mass spectrum m/e: 529 (MH+).

EXAMPLE 8

Preparation of 1,3 (p-N-isopropylcarbamoyl-benzylidene)-2,4-(p-methylbenzylidene)sorbitol Into a 200-ml flask were introduced 36.4 g (0.2 mol) of D-sorbitol, 24 ml of water, 24.0 g (0.2 mol) of p-tolualdehyde and 2.3 g (0.012 mol) of p-toluenesulfonic acid monohydrate. The resulting mixture was stirred at 35° C. for 6 hours under a nitrogen atmosphere, and then cooled to 20° C. To the thus-obtained reaction mixture in its white creamy state were added 100 ml of water and 0.5 g of sodium hydroxide, and the mixture was stirred at room temperature. The resulting white slurry was filtered to obtain a white solid. This white solid was washed with water and ether, and dried, thereby obtaining 48.8 g of 2,4-(p-methylbenzylidene)-sorbitol as a white powder in a yield of 85.9%.

Next, into a 2 -liter flask equipped with a Dean-Stark-type fractionating column and a powerful stirrer were introduced 48.8 g (0.17 mol) of the above-obtained 2,4-(p-methylbenzylidene)sorbitol, 32.5 g (0.17 mol) of p-(N-isopropylcarbamoyl)benzaldehyde, 800 ml of benzene and 0.32 g (1.7 mmol) of p-toluenesulfonic acid monohydrate. The resulting mixture was heated, with stirring, under reflux of the benzene at 77° C. for 6 hours under a nitrogen atmosphere. During the reaction, the water distilled out in the fractionating column was removed occasionally. After completion of the reaction, the reaction mixture was cooled to room temperature. Subsequently, to the resulting reaction mixture in its white gelatinous state were added 300 ml of water and 70 mg of sodium hydroxide, and the mixture was then stirred at room temperature. The resulting white slurry was filtered to obtain a white solid. The white solid thus obtained was washed with water and ethanol each having a temperature of about 70° C., and dried, thereby obtaining 72.2 g of the intended compound, 1,3-(p-N isopropylcarbamoylbenzylidene)-2,4-(p-methyl-benzylidene)sorbitol, as a white power in a yield of 92.9%. The yield as calculated on the basis of the D-sorbitol was 79.8%.

The analytical data for this compound were as follows:

Melting point 172.0°–175.0° C.

$^1$H-NMR spectrum (DMSO-$d_6$) $\delta$ [ppm]: 8.16(1H, broad-s), 7.83–7.88(2H, m), 7.49–7.56(2H, m), 7.32–7.36(2H, m), 7.16–7.20(2H, m), 5.60–5.85(9H, m), 2.31(3H, s), 1.17(6H, d).

FAB-Mass spectrum m/e: 458 (MH+).

APPLICATION EXAMPLE 11

6 g of the 1,3:2,4-bis(p-N-cyclohexylcarbamoylbenzylidene)sorbitol as obtained in Example 6 was dissolved in 100 g of N,N-dimethylformamide at 90° C. The resulting solution was cooled to room temperature and allowed to stand overnight, thereby obtaining a gel of N,N-dimethylformamide.

APPLICATION EXAMPLE 12

4 g of the 1,3:2,4-bis(p-N isopropylcarbamoylbenzylidene)sorbitol as obtained in Example 7 was dissolved in 100 g of N,N-dimethylformamide at 90° C. The resulting solution was cooled to room temperature and allowed to stand overnight, thereby obtaining a gel of N,N-dimethylformamide.

APPLICATION EXAMPLE 13

5 g of the 1,3-(p-N-isopropylcarbamoyl-benzylidene)-2,4-(p-methylbenzylidene)sorbitol as obtained in Example 8 was dissolved in 100 g of N,N-dimethylformamide at 90° C. The resulting solution was cooled to room temperature and allowed to stand overnight, thereby obtaining a gel of N,N-dimethylformamide.

APPLICATION EXAMPLE 14

A 20 wt % of tetramethylammonium hydrogenphthalate solution in γ-butyrolactone was prepared as an electrolyte for low-tension aluminum electrolytic capacitors. This electrolyte had an electrical conductivity as measured at 25° C. of 10.0 mS/cm and a sparking voltage, as measured with 5 mA/cm² of constant current applied to a pair of flat aluminum foils, + and −, of 90 V.

In this electrolyte was dissolved, by heating, 1,3:2,4-bis(p-methoxycarbonylbenzylidene)sorbitol [the compound of the formula (I) in which $X^1$ and $X^2$ were —COOCH$_3$ (p-position)] in such an amount that the concentration of this gelatinizer in the resulting solution became 1 wt %. The resulting solution was then cooled to obtain a transparent gel. The electrical conductivity and sparking voltage of this gel were 9.6 mS/cm and 90 V, respectively.

Figure 1:
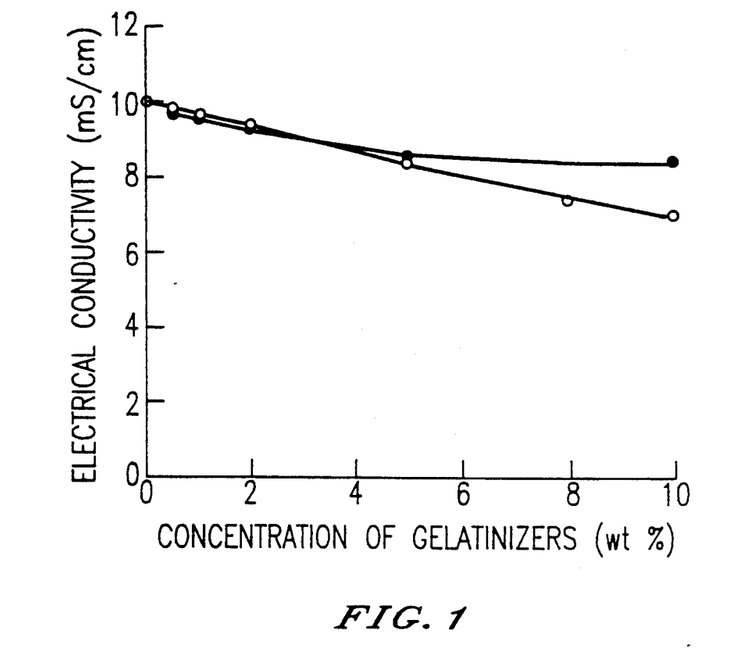
FIG. 1 is a graph showing the relationship between the amounts of gelatinizers added to a 20-wt % tetramethylammonium hydrogenphthalate solution in γ-butyrolactone and the electrical conductivity of the solution.

Likewise, electrical conductivities were measured with respect to samples having different concentrations of the gelatinizer. The results obtained are shown by means of  in FIG. 1.

REFERENCE APPLICATION EXAMPLE 1

The same procedures as in Application Example 14 were repeated except that 1,3:2,4-dibenzylidenesorbitol [a compound having such a structure that both $X^1$ and $X^2$ in formula (I) are —H] was used as a gelatinizer. As a result, it was found that the electrolyte was gelatinized only when the concentration of the gelatinizer was as high as 10% by weight. The electrical conductivity and sparking voltage of the electrolyte having a gelatinizer concentration of 10wt % were 7.0 mS/cm and 90 V, respectively. The relationship between the concentration of the gelatinizer and the electrical conductivity was shown by means of  in FIG. 1.

Application Example 15 and Reference Application

EXAMPLE 2

Figure 2:
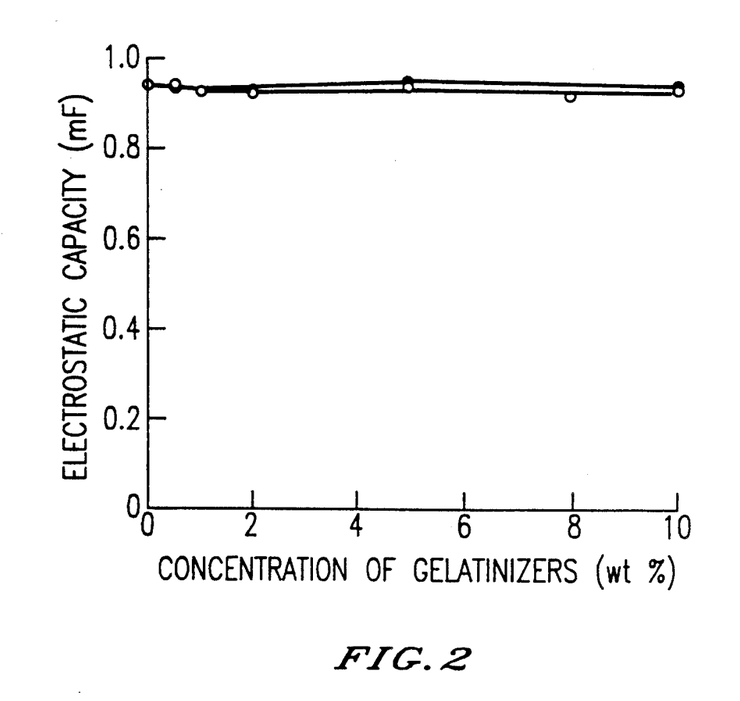
FIG. 2 is a graph showing the relationship between the electrostatic capacity of aluminum electrolytic capacitors employing the above electrolytes and the amount of gelatinizers.
Figure 3:
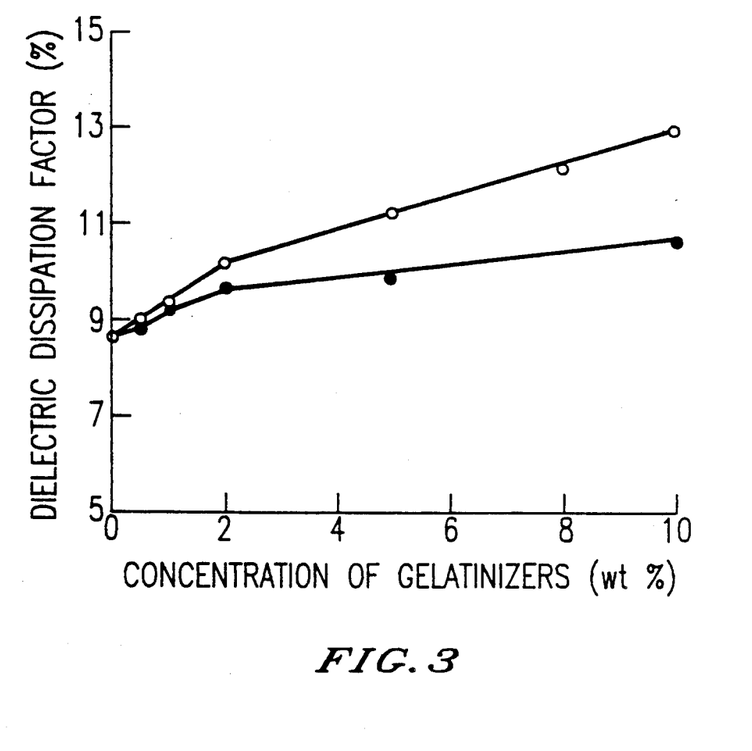
FIG. 3 is a graph showing the relationship between the dielectric dissipation factor of the capacitors and the amount of gelatinizers.

Using each of the electrolytes as prepared in Application Example 14 and those prepared in Reference Application Example 1, aluminum electrolytic capacitors (25V/1mF) were prepared. The electrostatic capacities, C, as measured at 120 Hz and the dielectric dissipation factors, tan δ, of these aluminum electrolytic capacitors were measured. The results obtained were shown in FIGS. 2 and 3, with •————• indicating the results of Application Example 15 and o————o indicating those of Reference Application Example 2. It was found that even in their gelatinous state, the electrolytes maintained their close contact with the aluminum electrodes, and no decrease in electrostatic capacity was observed. FIG. 3 shows that the electrolytic capacitors of the present invention (Application Example 15) had high performance with lower dielectric dissipation factors than those of the capacitors of Reference Application Example 2.

APPLICATION EXAMPLE 16

In the same electrolyte as used in Application Example 14 was dissolved, by heating, 1,3-(p-methoxycarbonylbenzylidene)-2,4-benzylidenesorbitol [the compound of formula (I) in which $X^1$ was —CO$_2$CH$_3$ (p-position) and $X^2$ was —H (p-position)] in such an amount that the concentration of this compound in the resulting solution became 2 wt %. The resulting solution was then cooled to obtain a transparent gel. The electrical conductivity of this gel was 17.6 mS/cm.

APPLICATION EXAMPLE 17

A 1M lithium perchlorate solution in a mixed solvent composed of propylene carbonate and 1,2-dimethoxyethane (1:1 by volume) was prepared as an electrolyte for manganese dioxide/lithium cells. This electrolyte had an electrical conductivity as measured at 25° C. of 13.5 mS/cm.

To this electrolyte was added 1,3-(p-methoxycarbonylbenzylidene)-2,4-dibenzylidenesorbitol in such an amount that the concentration of this compound in the resulting solution became 1 wt %, to gelatinize the electrolyte. The electrical conductivity of this gel was 12.9 mS/cm. Further, lithium was placed in this gel and the reactivity between them was observed. As a result, they were found to be stable, with no evolution of gases and change in color.

APPLICATION EXAMPLE 18

In 3.03 g (60.5 wt % based on the final polymer-gel electrolyte) of γ-butyrolactone was dissolved 0.6 g (12 wt %) of lithium perchlorate. To the resulting electrolyte was added 0.075 g (1.5 wt %) of the same sorbitol compound as prepared in Example 1. The resulting mixture was stirred and then heated to 70° C., and this temperature was maintained for 3 hours, thereby dissolving the sorbitol compound completely. Subsequently, to the thus-obtained solution was added 1.3 g (26.0 wt %) of methoxypolyethylene glycol methacrylate (n≐23) as a polymerizable vinyl monomer, followed by 4 mg of a polymerization initiator, Perbutyl-O (PBO; manufactured by Nippon Oil & Fats Co., Ltd., Japan). The resulting mixture was stirred to form a uniform solution.

. On the other hand, a cell having a capacity of 2 cm (width)×5 cm (length)×1 mm (thickness) was prepared by the use of a polyester film, glass plates and a 10-mm silicone sheet (the polyester film covered the inner walls of the cell and the silicone sheet served as a spacer). Part of the solution prepared above was poured into this cell, and polymerization was carried out at 80° C. for 16 hours under a nitrogen atmosphere. Thus, a polymer-gel electrolyte composition was obtained in the form of a sheet. The composition thus obtained was a colorless transparent gel with good flexibility and had an ionic conductivity of 1.6 mS/cm. Further, this composition was subjected to a heat cycle test (each cycle consisting of 110° C.×20 hours+room temperature×4 hours), and as a result it showed a heat resistance of 350 hours or more.

REFERENCE APPLICATION EXAMPLE 3

The same procedures as in Application Example 18 were repeated except that 0.60 g (12 wt %) of 1,3:2,4-dibenzylidenesorbitol was used as a sorbitol compound. Thus, a gelatinous electrolyte was obtained in the form of a sheet. At least 10 wt % of 1,3:2,4-dibenzylidenesorbitol was required to gelatinize the electrolyte. The gelatinous electrolyte sheet obtained had an ionic conductivity of 0.7 mS/cm.

REFERENCE APPLICATION EXAMPLE 4

The same procedures as in Application Example 18 were repeated except that no sorbitol compound was used, thereby obtaining a transparent gelatinous electrolyte composition in the form of a sheet. The thus-obtained composition had an ionic conductivity of 1.8 mS/cm. Further, this composition was subjected to the heat cycle test and, as a result, bubbles were produced 120 hours after the initiation of the test.

While the invention has been described in detail and with reference to specific embodiment thereof, it will be apparent to one skilled in the art that various changes and modifications can be made therein without departing from the spirit and scope thereof.

What is claimed is:

1. A dibenzylidenesorbitol derivative represented by the formula (I):

wherein one of $X^1$ and $X^2$ represents —$COOR^1$ and the remainder represents —$COOR^1$, or —$CONR^2R^3$, wherein $R^1$ represents a hydrocarbon group having 1 to 20 carbon atoms, and $R^2$ and $R^3$ are identical or different and each independently represents a hydrogen atom, and alkyl group, an aryl group or an aralkyl group.

2. A dibenzylidenesorbitol derivative according to claim 1, wherein both $X^1$ and $X^2$ represent —$COOR^1$.

3. A dibenzylidenesorbitol derivative according to claim 1, wherein one of $X^1$ and $X^2$ represents —$CONR^2R^3$.

4. The dibenzylidenesorbitol derivative of claim 1, wherein $R^1$ is methyl.

5. The dibenzylidenesorbitol derivative of claim 2, wherein $R^1$ is methyl.

6. The dibenzylidenesorbitol derivative of claim 3, wherein $R^1$ is methyl.

* * * * *